(12) United States Patent
Qin

(10) Patent No.: US 8,419,961 B2
(45) Date of Patent: Apr. 16, 2013

(54) OIL/GAS SEPARATION MEMBRANE, ITS USE IN GAS SENSOR AND PROCESS FOR PRODUCING THE SAME

(75) Inventor: Ren Yan Qin, Guangdong (CN)

(73) Assignee: Asensou Technologies Co., Ltd., Shenzhen, Guangdong (CN)

( * ) Notice: Subject to any disclaimer, the term of this patent is extended or adjusted under 35 U.S.C. 154(b) by 90 days.

(21) Appl. No.: 12/455,154

(22) Filed: May 28, 2009

(65) Prior Publication Data

US 2009/0255900 A1 Oct. 15, 2009

Related U.S. Application Data

(62) Division of application No. 10/971,443, filed on Oct. 21, 2004, now Pat. No. 7,811,362.

(30) Foreign Application Priority Data

Oct. 24, 2003 (CN) .......................... 2003 1 0111953

(51) Int. Cl.
*B32B 37/00* (2006.01)

(52) U.S. Cl.
USPC ................. 216/83; 216/52; 216/67; 156/153; 156/154; 156/60; 96/6; 96/11; 96/12; 95/46; 210/640

(58) Field of Classification Search .................. 96/6, 11, 96/12; 216/52, 67, 83; 156/153, 154, 60; 95/46; 210/640
See application file for complete search history.

(56) References Cited

U.S. PATENT DOCUMENTS

| | | | | |
|---|---|---|---|---|
| 2,984,599 A | * | 5/1961 | Edwards et al. | 156/333 |
| 3,556,305 A | * | 1/1971 | Shorr, Jacob | 210/490 |
| 5,462,781 A | * | 10/1995 | Zukowski | 428/36.1 |
| 6,228,146 B1 | * | 5/2001 | Kuespert | 95/46 |
| 6,526,805 B1 | * | 3/2003 | Marusic et al. | 73/19.12 |
| 7,811,362 B2 | * | 10/2010 | Qin | 204/295 |
| 2003/0054110 A1 | * | 3/2003 | Yamaguchi et al. | 427/420 |
| 2003/0207167 A1 | * | 11/2003 | Prakash et al. | 429/42 |

OTHER PUBLICATIONS

A. A. Benderly, "Treatment of Teflon to Promote Bondability", J. Appl. Polymer Science, vol. 6, p. 221 (1962) Wiley.*

* cited by examiner

*Primary Examiner* — Lan Vinh
*Assistant Examiner* — David Kaufman
(74) *Attorney, Agent, or Firm* — Raymond Y. Chan; David and Raymond Patent Firm

(57) ABSTRACT

An oil gas separation membrane combines a gas permeable yet oil and temperature resistant bulk polymer membrane such as poly(tetrafluoroethylene) and poly(tetrafluoroethylene-co-hexafluoropropylene); a porous metal support such as sintered metal frit disk made with stainless steel, bronze or nickel; and an highly gas permeable adhesive that bonds firmly the bulk polymer membrane and the metal frit surface together. The adhesive is either a homogenous polymer that has desirable gas permeability, or a coalescent porous polymer particulates network. A gas sensor employing the oil gas separation membrane for detecting and monitoring fault gases of oil filled electrical equipment requires no mechanical wearing or moving part such as pump and valve and the gas sensor is operated normally under various temperature and pressure conditions.

7 Claims, 5 Drawing Sheets

OIL/GAS SEPARATION MEMBRANE, ITS USE IN GAS SENSOR AND PROCESS FOR PRODUCING THE SAME

CROSS REFERENCE OF RELATED APPLICATION

This is a divisional application of a non-provision application having an application Ser. No. of 10/971,443 and a filing date of Oct. 21, 2004 now U.S. Pat. No. 7,811,362.

BACKGROUND OF THE PRESENT INVENTION

1. Field of Invention

This invention relates to on-line detection and monitoring method and apparatus of oil-filled electric equipments, more particularly, relates to an oil/gas separation membrane applied for monitoring fault gas within the oil-filled electric equipments, a method for preparing such oil/gas separation membrane, as well as a gas sensor equipped with such oil/gas separation membrane.

2. Description of Related Arts

Generally, Oil-filled electric equipment refers to those electric equipments employing dielectric liquid (i.e. insulating oil) as dielectric medium, such as transformer, shunt reactor, tap changer and so on. Needless to say, a reliable and safe operation of these important equipments is the key factor for ensuring efficient power generation, transmission and distribution.

For instance, the incipient fault detection and monitoring system for a transformer could significantly reduce the operational accidents, improve the reliability of power grid and provide a safer working environment of substation. There are several monitoring methods and parameters for on-line monitoring of the incipient fault of a transformer, for instance, monitoring of dissolved gas in oil, monitoring of partial discharge, monitoring of oil temperature and leaking current detection. So far, the monitoring of the gases dissolved in oil is still the most important and reliable method for detecting the incipient fault. This is due to the fact that a symptom of gas in the oil is a first indicator of transformer fault development.

When a fault is developed in a transformer, an immediate consequence would be a local overheating or a local electric discharging accompanied with high energy releasing. As a result, the insulating oil and paper positioned close to the fault point would be broken down by the high temperature to generate a variety of gases and other substances. These fault gases (i.e. gases generated followed the faults condition) comprise hydrogen (H2), carbon monoxide (CO), ethylene (C2H4) and acetylene (C2H2), often called key gases in fault conditions. Statistics shows that there is a direct relationship between the type & content of the fault gas and the nature & intensity of the fault. It is seen that the analysis of dissolved gases in transformer oil was analog to the analysis of sampled human blood.

Conventionally, the dissolved gas analysis (e.g. DGA) procedures are accomplished in laboratory, and the procedure comprises scheduled on-site sampling, degassing and gas chromatograph analysis in laboratory. Until recently, the DGA is still the most popular method for transformer maintenance worldwide. However, this method still suffers an obvious drawback. Commonly, DGA was taken based on a referenced schedule, for example, from three months to a full year time period. Therefore, it is powerless to detect those faults developed quickly between two scheduled analysis time period.

In order to improve the efficiency, a new monitoring method, namely status based maintenance (or on-line monitoring and detection) has been introduced within the art. According to this new method, the real time on-line monitoring system is capable of continuously monitoring the fault gases dissolved in transformer oil without affecting the normal operation of the transformer. In addition, by comparing and analyzing the historical monitoring data, this new method is capable of providing an evolution and trend of fault gases status, therefore providing the user with first hand and accurate information.

FIG. 5 is a schematic diagram illustrating a typical transformer on-line monitoring system, wherein fault gases generated within the transformer 50 is delivered to transformer valve 501 via oil circulation, and then is directed to the gas sensor 511 so that a monitoring signal is collected, conditioned and managed by microprocessor 512 (gas sensor 511 and microprocessor 512 together forms signal transmitter 51), afterwards, the final monitoring data is transmitted to host 53 via communication controller 52, and the monitoring data can further be transmitted to a data server 54 and an expert system web 55. It is noted that the gas sensor 511 is directly connected to the transformer valve 501, which is adapted for directly separating the fault gas from the oil, and then sampling the fault gas so as to generate a monitoring signal.

It is obvious that the key technology behind the transformer on-line monitoring is the oil/gas separation and gas sensing. Since gas sensor is off limited with the oil, the oil/gas separation becomes primarily important in on-line monitoring system.

In U.S. Pat. No. 4,112,737, James E. Morgan disclosed a method and apparatus for monitoring the fault gases of transformer. According to Morgan's invention, a polymer hollow fiber bundle is utilized as a gas separator. The advantage of this method is that the hollow fiber has a higher surface/volume ratio so as to withstand negative pressure through deformation. The drawback is that the separated gases must be carried away by a carrier (usually use dry air or inert gas) or a gas pump to reach the sensing element or a sensing device. Therefore the complicated whole system will more or less reduce the reliability.

In U.S. Pat. No. 4,293,399, Guy Belanger et al. disclosed an apparatus for detecting the hydrogen dissolved in transformer oil. The apparatus comprises a fuel cell (electrochemical) type sensor which is disposed within a gas chamber and is positioned next to a polymer separation membrane. One side of the membrane is in direct contact with the transformer oil, and the another side is close to the sensing electrode. So that hydrogen dissolved in the oil is capable of being separated by the membrane to reach the sensor. The advantage of this method is that the gases can permeate through the membrane and reach the sensing element on their own, thus avoiding the use of gas pump or carrier gas. The drawback is that the thin polymer membrane is venerable to deformation and damage under condition of negative pressure (vacuum) and high temperature, resulting in the drift of sensor calibration, and to a worse extent, resulting to oil leaking as well as the permanent damage of the sensor.

In U.S. Pat. No. 5,749,942, John Seymour Mattis et al. disclosed a method of making a composite membrane in which a very thin layer of an amorphous perfluoro-2,2-dimethyl-1,3-dioxole polymer is supported on a porous support membrane such as vinylidene difluoride homopolymer or copolymer. Even such membrane is stronger than the unsupported one, but is still fragile and subject to the deformation and damage under harsh conditions (temperature and pressure).

Also in U.S. Pat. No. 5,749,942, John Seymour Mattis et al disclosed a method and an apparatus for transformer oil/gas separation, in which the fragile polymer membrane is sandwiched between a perforated metal plate or a wire screen or mesh. This method is effective for preventing the deformation of polymer membrane to some extent, but is still less satisfied for resolving the fundamental problem mentioned above. Moreover, the covering of the metal plate or screen on the membrane surface will impair the oil convection over the membrane and reduce the contact surface of the membrane, therefore negatively affecting the separation efficiency. Furthermore, the extracted or separated gases have to be delivered to a separated gas collection station for gas analysis by a gas circulation device such as a pump. This further reduces the reliability of the system.

Conclusively, it is desirable to develop an oil/gas separation membrane and a gas sensor, which is capable of being applied in a relative harsh working condition, such as high temperature, high pressure, and negative pressure, and without having to use various mechanical wearing and moving parts such as pump and valve, so as to improve the reliability of gas monitoring system within the art.

SUMMARY OF THE PRESENT INVENTION

A primary object of the present invention is to provide an oil/gas separation membrane for solving above mentioned drawbacks of fault gas detection/monitoring system, wherein the oil/gas separation membrane is capable of withstanding high temperature and negative pressure (i.e. vacuum) without losing mechanical property and permeation efficiency.

Another object of the present invention is to provide a method for preparing the above mentioned oil/gas separation membrane.

Another object of the present invention is to provide a gas sensor for detecting and monitoring fault gas of oil-filled electric systems, wherein no complicated mechanical wearing and moving parts such as pumps and valves are applied, and in the mean time the gas sensor is capable of operating normally under various temperature and pressure conditions.

Accordingly, to achieve the above mentioned objects, the present invention provides an oil/gas separation membrane, comprising a gas permeable bulk polymer membrane, a porous sintered metal frit, and a gas permeable adhesive for bonding the gas permeable bulk polymer and the porous sintered metal frit together.

The present invention further provides a method of making the oil/gas separation membrane, the method comprising:

Preparing a bulk polymer membrane with the thickness between 0.01-0.5 mm from a polymer material selected from a group consisting of PTFE, PVDF, PFEP, and PFA;

providing a metal frit disk made of metal selected from a group consisting of stainless steel, copper and nickel, with a metal frit thickness between 1-5 mm, porosity greater than 20% and pore size between 0.001-0.1 mm;

preparing an adhesive which is selected from a group consisting of organic solution of TFE/PFD copolymer, aqueous solution of PTFE or PFEP particulate dispersion, and organic solution of PTFE or PFEP particulate dispersion with 0.05-5 µm in particle size; and bonding the polymer membrane and the metal frit disk with the adhesive and baking at a predetermined temperature.

The present invention further provides a gas sensor for detecting fault gases of oil filled electrical equipment, which comprises:

a sensor body having a first end connected with the oil filled electrical equipment, and a receiving cavity;

a gas/oil separation membrane received in the receiving housing, comprising a gas permeable bulk polymer membrane orientated towards the first end, a porous sintered metal frit, and a gas permeable adhesive for bonding the gas permeable bulk polymer and the porous sintered metal frit together; and a gas sensitive element disposed next to the porous sintered metal frit for detecting a presence of the fault gases and outputting a corresponding signal through a metal wire.

These and other objectives, features, and advantages of the present invention will become apparent from the following detailed description, the accompanying drawings, and the appended claims.

DETAILED DESCRIPTION OF THE PREFERRED EMBODIMENT

Figure 1A:
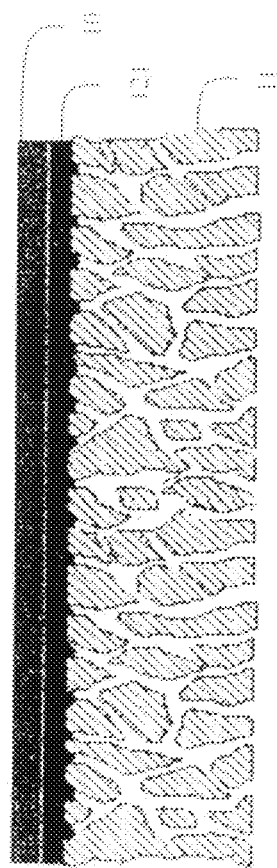
FIGS. 1a and 1b are schematic views illustrating an oil gas separation membrane according the preferred embodiment of the present invention.

Referring to FIG. 1 to FIG. 5, the oil/gas separation membrane according to the preferred embodiment of the present invention is illustrated.

The present invention provides an oil/gas separation membrane, comprising a gas permeable bulk polymer membrane 10, a porous sintered metal frit 11, and a gas permeable adhesive 121 and 122 for bonding the gas permeable bulk polymer membrane 10 and the porous sintered metal frit 11 together.

The "bulk" membrane in this invention relates to nonporous membrane where the gas permeation mechanism is molecule adsorption, dissolution, diffusion and desorption across the membrane. It is fundamentally different from porous membrane reported in the literature where the gas separation is achieved through molecule sieve mechanism.

According to the present invention, the bulk polymer membrane is made of polymer material selected from a group consisting of poly(tetrafluoroethylene) (PTFE), poly(tetrafluoroethylene-co-hexafluoropropylene) (PFEP), poly(vinylidene fluoride) (PVDF), and poly(tetrafluoroethylene-co-perfluoro alkoxy vinyl ether) (PFA).

The porous metal support is in form of sintered powder metal frit made of metals selected from a group consisting of stainless steel, bronze and nickel. The adhesive has permeability at least 50 times greater than the bulk gas permeable membrane. It is made either with highly gas permeable amorphous polymer dissolved in organic solvent, or with fine polymer particulates suspended in water and/or organic solvent.

According to the preferred embodiment of the present invention, the adhesive is a copolymer solution of TFE/PFD, i.e. (tetrafluoroethylene)/(2,2-bis-perfluoromethyl-4,5-difluoro-1,3-dioxole) dissolved in perfluorinated solvents, or the PTFE or PFEP particulate dispersion in water and/or organic solvent with 0.05-5 μm in particle size.

The present invention further provides a method of making the oil/gas separation membrane, the method comprises the following steps.

(a) Prepare a bulk polymer membrane with the thickness between 0.01-0.5 mm from a polymer material selected from a group consisting of PTFE, PVDF, PFEP, and PFA;

(b) Provide a metal frit disk made of metal selected from a group consisting of stainless steel, copper and nickel, with a metal frit thickness between 1-5 mm, porosity greater than 20% and pore size between 0.001-0.1 mm;

(c) Prepare an adhesive which is selected from a group consisting of organic solution of TFE/PFD copolymer, aqueous solution of PTFE or PFEP particulate dispersion, and organic solution of PTFE or PFEP particulate dispersion with 0.05-5 μm in particle size; and (d) Bond the polymer membrane and the metal frit disk with the adhesive and baking at a predetermined temperature.

In the step (d), the predetermined temperature could be set between 100-240° C. in case TFE/PFD copolymer is used as adhesive, or be set 120-350° C. in case PTFE or PFEP particulate dispersion is used as adhesive. It is noted that the final composite membrane is obtained with the thickness of the adhesive after drying between 0.005-0.05 mm.

According to the present invention, in the step (a), there is a further step for treating the bulk polymer membrane to increase the surface roughness. There is a plurality of measures to accomplish the surface treating as showing below.

(a-1) Sanding uniformly the bulk polymer membrane with #600-1500 abrasive paper;

(a-2) etching the bulk polymer membrane for 1-15 minutes with an etching solution formulated at weight ratio of sodium 1 part:Naphthalene 4 parts:Tetrahydrofuran 3 parts.

(a-3) bombarding the bulk polymer membrane surface with Argon or Nitrogen plasma gas under condition of 13.56 MHz RF, 100-500 W power source, 0.5-50 Pa pressure and 10-30 minutes radiation time.

The present invention further provides a gas sensor for detecting a fault gases of an oil filled electrical equipment, which comprises a sensor body having a first end connected with the oil filled electrical equipment, and a receiving cavity.

The gas sensor further comprises a gas/oil separation membrane received in the receiving housing, comprising a gas permeable bulk polymer membrane orientated towards the first end, a porous sintered metal frit, and a gas permeable adhesive for bonding the gas permeable bulk polymer and the porous sintered metal frit together.

Finally, the gas sensor comprises a gas sensitive element disposed next to the porous sintered metal frit for detecting a presence of the fault gases and outputting a corresponding signal through a metal wire.

According to the present invention, the gas sensitive element is preferably an electrochemical/fuel cell gas sensor. The fuel cell type sensor possesses excellent properties such as high sensitivity to fault gases, quick response time, broad dynamic response range, good stability and repeatability. The principle of fuel cell operation is that the fault gases are oxidized by an electrocatalyst at anode and release electrons; while the oxygen in air are reduced by an electrocatalyst at cathode and accept the electrons, and a current will flow and will be proportional to the gas concentration when the anode and the cathode are connected with an external circuit. In practice, a load resistor is employed for the convenience of voltage measurement.

According to the present invention, two types of electrochemical/fuel cell gas sensors based on electrode and electrolyte difference are covered: one employs gas diffusive electrodes and liquid electrolyte, wherein the gas diffusive electrodes are made with porous carbon paper and metal catalyst loaded on carbon black, the metal catalyst being composed of one of or the combination of Platinum, Ruthenium, Rhodium and gold metal; and the electrolyte being in form of gel is composed of sulfuric acid or phosphorous acid and porous SiO2 powder.

The second one employs porous metal electrodes and solid electrolyte, wherein the porous metal electrodes are made by chemically depositing the nanoscale metal particles on a solid polymer electrolyte membrane. The metal catalyst is composed of one of or the combination of Platinum, Ruthenium, Rhodium and Gold metal; and the solid polymer electrolyte membrane is a proton exchange membrane such as the copolymer of tetrafluoroethylene and perfluoro-3,6-dioxa-4-methyl-7-octene-sulfonic acid under the tradename Nafion from E.I. Du Pont de Nemours and Company.

The resistive or field-effect type gas sensor made with palladium or palladium alloyed with Pt, Au, Ag and Ni resistor in form of wire or membrane (based on resistance change upon hydrogen absorption), or in form of catalytic metal gate in field-effect metal oxide semiconductor (MOSFET), or metal oxide semiconductor (MOS) gas sensor are less stable and efficient, but still covered by the present invention.

The MOSFET sensor is based on the fact that the adsorbed hydrogen atoms are polarized at metal oxide interface and create a layer of dipoles at the interface, this layer in turn causes a shift of electrical characteristics (e.g. threshold voltage) of the structure.

The MOS sensor is based on the fact that the presence and the following oxidation of fault gases change the electrical barrier at the boundary of microcrystallines, thus the conductivity.

On one side of the sensor body, the oil gas separation membrane is sealed to internal part of the sensor body by an O-ring made with oil-resistant perfluorocarbon rubber to prevent the oil from penetrating into the gas sensitive element.

On the other side of the sensor body, there is a sensor cover on which an oxygen permeable membrane is sealed through an O-ring. The said oxygen permeable membrane allows to supply the oxygen from the air to the counter (cathode) electrode, while restricting the water vapor exchange. It is made with bulk polymer materials having high oxygen/water vapor permeation ratio, which is greater than 0.03, and having thickness between 0.005-0.1 mm. These polymer materials include PTFE, polyethylene (PE) and polypropylene (PP).

In accordance with the present invention, the said oil/gas separation membrane keep desired gas permeability of the bulk polymer membrane, therefore can effectively separate the fault gases from the oil; in the mean time, with metal disk reinforcement, it resists the deformation and damage under high temperature and negative pressure.

The gas sensor such made can be applied to fault gas detection and monitoring without having to use various mechanical wearing and moving parts such as pumps and valves, and in the mean time can operate normally under various temperature and pressure conditions.

EXAMPLES

Objects and advantages of this invention are further illustrated by the following examples, but the particular materials and amounts thereof recited in these examples, as well as other conditions and details, should not be construed to unduly limit this invention.

Example 1

Bulk polymer membrane: the selected membrane must be stable, oil-resistant, temperature-resistant, permeable to fault gases and impervious to oil. In practice, PTFE, PVDF, PFEP, and PFA are good choices. According to the preferable embodiment, PTFE membrane obtained from Saint-Gobain Advanced Materials, Taiwan is applied. It is worth to mention that thickness of the membrane is ranged between 0.01 to 0.5 mm, preferably, ranged between 0.025 to 0.125 mm.

Example 2

Porous metal frit disk: the selected porous metal frit disk is prepared by metal powders under a high temperature and a high pressure circumstance. It is noted that the metal frit disk must have a good mechanical strength to support the bulk polymer membrane, and a high porosity to allow quasi resistant-free gas permeation.

In practice, the stainless steel, bronze and nickel are good choices. The preferred embodiment of the present invention utilizes the sintered stainless steel frit disk obtained from GKN Sinter Metals, Germany, with the porosity greater than 20%, preferably between 35-55%, pore size between 0.001-0.1 mm, preferably between 0.005-0.02 mm, and thickness between 1-5 mm.

Example 3

Adhesive: the selective adhesive must have good chemical compatibility with the polymer membrane and porous metal frit, and more importantly have extremely high gas permeability so that the presence of this adhesive will affect very little, if not, the overall gas permeation. There are two preferred embodiments in the present invention:

First, a solution made with amorphous high permeable polymer, namely (tetrafluoroethylene)/(2,2-bis-perfluoromethyl-4,5-difluoro-1,3-dioxole) copolymer, or P (TFE/PFD) from E.I. Du Pont de Nemours and Company, Wilmington, Del. The copolymers are available under the Trade Name "Teflon AF" in grades such as 1600 and 2400, having Tg's of 160 and 240° C., respectively. The difference between Teflon AF 2400 and Teflon AF 1600 is in their mole ratio of TFE/PFD which are 13%/87% and 35%/65%, respectively. Teflon AF has permeability 1-2 magnitudes higher than bulk PTFE membrane, taking hydrogen as an example, the H2 permeability in PTFE is 7.4 Barrer at 25° C. (J. Brandrup et al., Polymer Handbook, 4th Edition, p. VI/552, John Wiley & Sons) while it is 2400 Barrer in Teflon AF2400 (A. Y. Alentiev et al., Journal of Membrane Science, 126 (1997), p 123-132). The latter has permeability 324 times higher than bulk PTFE membrane; therefore it has very little influence in overall gas permeation as an adhesive. When the copolymer solution is used as an adhesive for bulk PTFE membrane and the metal frit, it has to be baked at a temperature between 100-240° C. with the thickness of 0.005-0.05 mm after drying. The Teflon AF has been patented as a gas extraction membrane in the prior art (U.S. Pat. No. 5,749,942), but it is unsuitable to apply to the preferred embodiment because Teflon AF also has very high permeability of water vapor (4026 Barrer for Teflon AF2400). It could quickly dry up the electrolyte, thus reduce the sensor life, not to mention the fragility of the Teflon membrane itself.

Second, a dispersion made with PTFE particulates obtained from DuPont under the Trade Name "Teflon PTFE Grade 30". It contains 60% by weight of PTFE particles with 0.05-5 μm in particle size dispersed in water and wetting agent. When used as an adhesive, it has to be baked at a temperature between 120-350° C. to form a coalesced porous network. The porous layer so formed has much higher gas permeability than the bulk PTFE membrane, therefore it has very little influence in overall gas permeation as an adhesive.

Example 4

Surface treatment of bulk polymer membrane: the adhesion force between the adhesive mentioned in Example 3 and bulk polymer membrane mentioned in Example 1 is principally based on "anchoring" effect or physical contact. Therefore, to obtain a better adhesion result, a surface treatment on bulk PTFE membrane is necessary to increase the surface area. According to the present invention, there are a plurality of treating methods shown below.

(A) sanding uniformly the bulk polymer membrane surface with #600-1500 abrasive paper, i.e. silicon carbide abrasive paper;

(B) etching the bulk polymer membrane for 1-15 minutes with an etching solution formulated at weight ratio of sodium 1 part:Naphthalene 4 parts:Tetrahydrofuran 3 parts.

(C) bombarding the bulk polymer membrane surface with Argon plasma gas under condition of 13.56 MHz RF, 100-500 W power source, 0.5-50 Pa pressure and 10-30 minutes radiation time.

Example 5

Figure 2A:
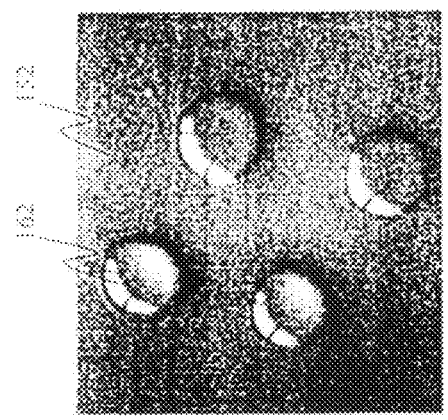
FIGS. 2a and 2b are schematic views illustrating the water droplet wetting on PTFE membrane surface before and after surface treatment with Argon plasma etching.
Figure 2B:
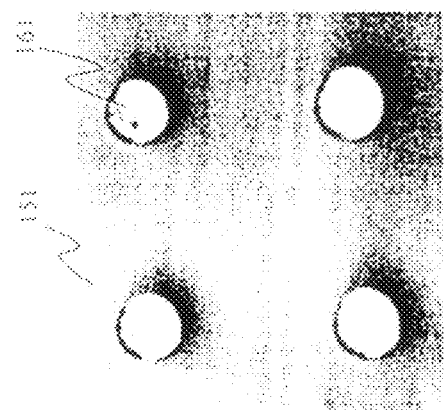

Wetting test with water droplets on bulk PTFE membrane surface before and after surface treatment with Argon plasma etching: a bulk PTFE membrane described in Example 1 (thickness 0.050 mm) is etched with Argon plasma described in Example 4 and tested with water droplets on wetting. FIGS. 2a and 2b show the difference of surface wetting before and after the treatment. In FIG. 2a, the water droplet 161 appears almost spherical on the untreated PTFE membrane 151, and the contact angle is greater than 100°; while in FIG. 2b the water droplet 162 spreads on the treated PTFE membrane 152, and the contact angle is much less than 100°. This demonstrates the effectiveness of Argon plasma treatment.

Example 6

Structure of the oil/gas separation membrane: FIG. 1a is a schematic illustration of a preferred embodiment of oil/gas separation membrane, wherein the adhesive used is a (PTFE/PFD) copolymer described in Example 3. In FIG. 1a, the bulk polymer membrane 10 is made with PTFE; the porous metal frit disk 11 is made of stainless steel; and the adhesive 121 is made with Teflon AF 1600.

Figure 1B:
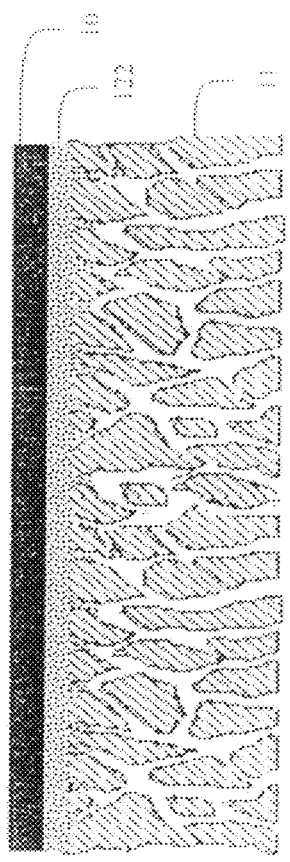

FIG. 1b is a schematic illustration of an another preferred embodiment of oil/gas separation membrane, wherein the adhesive 122 is made of Teflon PTFE 30 particulate dispersion with PTFE particle size of 0.05-0.5 μm.

Example 7

Gas permeation test—Test #1: 0.05 mm bulk PTFE membrane is manually sanded before use as described in Example 4, is then adhered to a 0.005 mm pore size stainless steel frit disk by using Teflon AF 1600 solution as adhesive. The other conditions are the same as described in Example 3. The final oil/gas separation membrane is obtained with the adhesive thickness of 0.005-0.01 mm.

Table 1 shows that If the relative permeability of the bulk PTFE membrane towards hydrogen gas is set at 1, the relative permeabilities of the final oil/gas separation membrane from sample A and sample B are 1.064 and 1.087, respectively, which are basically within experimental error.

TABLE 1

|  | Sample A | Sample B |
| --- | --- | --- |
| Bulk PTFE membrane permeation to $H_2$ | 1 | 1 |
| Final oil/gas separation membrane permeation to $H_2$ | 1.064 | 1.087 |

Test #2: Follow the same procedure and steps as Test #1 to prepare the oil/gas separation membrane (Sample C and Sample D) except that the membrane is pretreated with Argon plasma etching. Table 2 shows the results:

TABLE 2

|  | Sample C | Sample D |
| --- | --- | --- |
| Bulk PTFE membrane permeation to $H_2$ | 1 | 1 |
| Final oil/gas separation membrane permeation to $H_2$ | 0.846 | 0.925 |

Test #3: Follow the same procedure and steps as Test #2 to prepare the oil/gas separation membrane (Sample E and Sample F) except that the adhesive is Teflon PTFE 30. Table 3 shows the results:

TABLE 3

|  | Sample E | Sample F |
| --- | --- | --- |
| Bulk PTFE membrane permeation to $H_2$ | 1 | 1 |
| Final oil/gas separation membrane permeation to $H_2$ | 0.856 | 0.952 |

Example 8

Pressure test: the oil/gas separation membranes prepared in Test#1 thru Test#3 (i.e. Sample A through Sample F) are submitted to pressure from 1 Mpa (10 atms) positive to absolute vacuum (1 atm negative pressure) at room temperature. The membranes have no visible deformation or damage.

The Samples A through Sample F were placed into transformer oil at 60-70° C. for 12 months, during which the vacuum was applied regularly to the membranes. No visible deformation or damage has been observed.

However, serious permanent deformation takes place when the bulk PTFE membrane is submitted to the pressure test mentioned above.

Example 9

Gas sensor made with oil/gas separation membrane: in a gas sensor made with the oil/gas separation membranes described in the above examples, the membrane side should face the oil flow of transformer, to allow the fault gases dissolved in oil passing to the other side of the membrane through adsorption, dissolution, diffusion and desorption mechanism.

In practice, the oil/gas separation membrane is placed directly next to the sensing element (i.e. electrode), so that the fault gases separated from the membrane can quickly diffuse onto the sensing element. In general, the distance between the oil/gas separation membrane and the sensing element should be less than 5 mm, preferably less than 2 mm in order to ensure quick response time and improve analytical performance.

Figure 3:
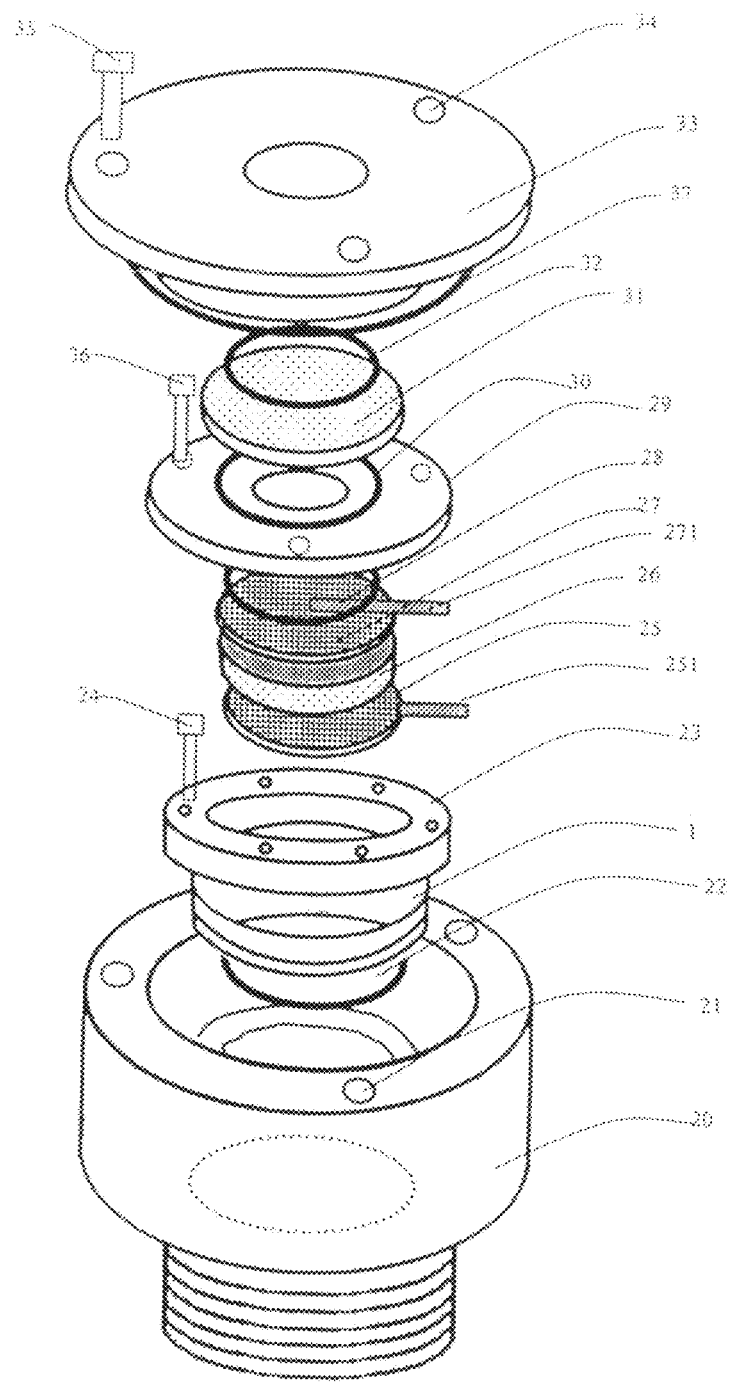
FIG. 3 is a schematic view illustrating the gas sensor which comprises an oil/gas separation membrane and a fuel cell type sensing element according to the preferred embodiment of the present invention.

FIG. 3 is a schematic illustration of a preferred gas sensor embodiment combining oil/gas separation membrane and fuel cell type sensing element in accordance with the present invention. In FIG. 3, one end of the sensor body 20 has male thread which can directly install to the transformer valve via a flan adaptor (not shown on the drawing).

The oil/gas separation membrane 1 is pressed from metal frit side onto the inside step of the sensor body 20 with a metal ring 23 and screws 24, and sealed with an oil resistant o-ring 22 (i.e. Viton rubber) to prevent the oil from penetrating.

The fuel cell 26 consists of an anode 25, an anode current collector 251, an electrolyte (not shown on the drawing), a cathode 27, and a cathode current collector 271. The fuel cell is assembled into the sensor body 20 with the help of cell cover 29, screws 36 and the metal ring 23.

The fault gases from transformer oil are separated from the oil/gas separation membrane 1, then reach the working electrode 25 (i.e. anode) of the fuel cell 26 wherein the gases are oxidized and the electrons are released; while the oxygen is reduced at the cathode and the electrons are accepted. The electrical signal generated is outputted to an external data acquisition device (not shown in the drawing) via current collectors 251 and 271 (i.e. Pt or Au wire) which have intimate contact to the anode 25 and cathode 27. The anode 25 and cathode 27 are gas diffusive electrodes made with porous carbon paper and metal catalyst loaded on carbon black, the metal catalyst being composed of one of or the combination of Platinum and Ruthenium metal. Both the carbon paper and metal catalyst are mixed with Teflon PTFE 30 to achieve the hydrophobic and porosity.

The fuel cell 26 uses an acidic electrolyte in form of gel, which is composed of sulfuric acid or phosphorous acid and porous $SiO2$ powder from Cabot Corporation under the trade name of "Car-O-Sil".

The cell cover 29 has a center hole where an oxygen permeable membrane 31 is fixed with the help of an O-ring 30. The oxygen permeable membrane 31 has two functions: one is to protect the fuel cell from external dust, particulate or liquid droplets; the another is to provide the cathode with oxygen necessary for the reaction, while restricting the water vapor exchange between the inside and the outside of the sensor. The oxygen permeable membrane 31 is selected based on its oxygen/water vapor permeability ratio, which should be higher than 0.03. PTFE, polyethylene (PE) and polypropylene (PP) are good choices. The preferred embodiment of the present invention is bulk PTFE membrane with thickness between 0.005-0.1 mm. At 25° C., the permeability of oxygen in bulk PTFE membrane is 3.2 Barrer, and that of water vapor is 6 Barrer, (J. Brandrup et al., Polymer Handbook, 4th Ed., P.VI/552, John Wiley & Sons, Inc., 1999), therefore the oxygen/water vapor permeability ratio is 0.53○

After all parts inside the sensor body 20 have been installed, the sensor cover 33 has a central hole and is fixed to the sensor body 20 with the help of threaded hole 21, cover hole 34 and screw 35. The sensor cover 33 is pressed to realize the sealing of the above-mentioned membrane 31 via the O-ring 32. The overall sealing between the sensor body 20 and sensor cover 33 is realized with the O-ring 37.

Example 10

Gas sensing test: the test is conducted by alternatively introducing the fresh oil (saturated only with the clean air) and the gas-contained oil (saturated with 2% H2 in nitrogen) into the gas sensor described in Example 9 at room temperature via an enclosed oil container and valves. The load resistor of the gas sensor is 499 Ohms.

Figure 4:
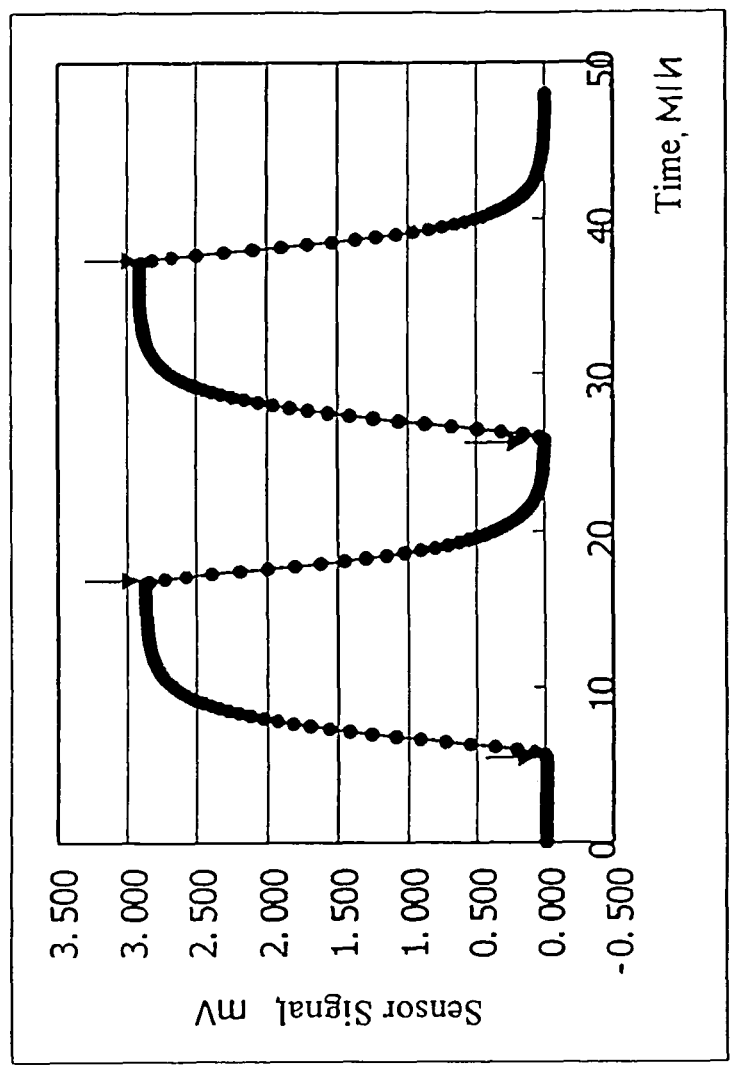
FIG. 4 is a schematic view of a response curve to hydrogen gas of the gas sensor.
Figure 5:
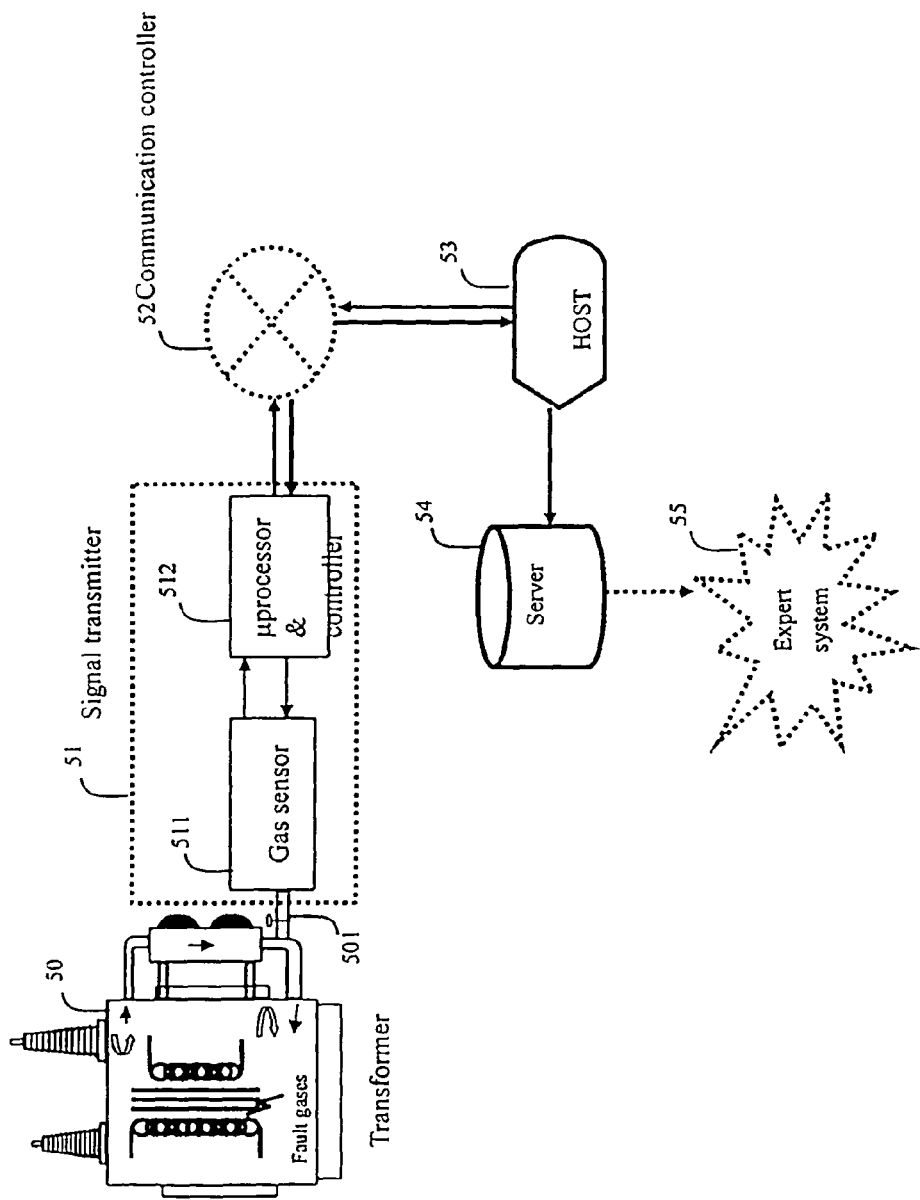
FIG. 5 is a schematic illustration of the principle of a typical on-line transformer monitoring system.

FIG. 4 is a schematic illustration of the response curve of the sensor embodiment shown in FIG. 3 versus hydrogen gas.

When the fresh oil is introduced into the sensor at the beginning of the test, the sensor signal is close to zero (offset);

When the gas-contained oil is introduced at $6^{th}$ minute, the sensor responds rapidly and reaches 2.8 mV and stabilized;

At $17^{th}$ minute with the reintroduction of the fresh oil, the sensor signal rapidly reduce to close zero and stabilized;

At $27^{th}$ minute with again the reintroduction of the gas-contained oil, the sensor again responds to 2.8 mV and stabilized;

The sensor has excellent response character and repeatability.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for preparing an oil gas separation membrane for separating dissolved fault gases from gas-containing dielectric fluid of an electric system, comprising the steps of:
    (a) preparing a bulk polymer membrane with a thickness between 0.01-0.5 mm from a polymer material
        wherein said bulk polymer membrane is sanded uniformly by #600-1500 abrasive paper, and
    etching said bulk polymer membrane for 1-15 minutes with an etching solution formulated at a weight ratio of sodium 1 part:Naphthalene 4 parts:Tetrahydrofuran 3 parts,
    wherein said bulk polymer membrane is made of material selected from the group consisting of poly(tetrafluoroethylene), poly(tetrafluoroethylene-co-hexafluoropropylene), poly(vinylidene fluoride), and poly(tetrafluoroethylene-co-perfluoro alkoxy vinyl ether);
    (b) providing a metal frit disk made of metal selected from the group consisting of stainless steel, copper, and nickel, with a metal frit thickness between 1-5 mm, porosity greater than 20%, and pore size between 0.001-0.1 mm;
    (c) preparing a gas permeable adhesive which is an amorphous polymer selected from the group consisting of an organic solution of TFE/PFD copolymer, an aqueous solution of PTFE or PFEP particulate dispersion, and an organic solution of PTFE or PFEP particulate dispersion with 0.05-5 μm in particle size; and
    (d) bonding said bulk polymer membrane and said metal frit disk with said gas permeable adhesive, and baking said bonded membrane at a predetermined temperature.

2. The method, as recited in claim 1, wherein said step (a) further comprises a step of bombarding the bulk polymer membrane surface with Argon or Nitrogen plasma gas under condition of 13.56 MHz RF, 100-500 W power source, 0.5-50 Pa pressure and 10-30 minutes radiation time.

3. The method, as recited in claim 1, wherein said organic solution of TFE/PFD copolymer has a mole ratio of TFE/PFD of 13%/87% or 35%/65%, and has a permeability 1-2 magnitudes higher than that of said bulk polymer membrane.

4. The method, as recited in claim 2, wherein said organic solution of TFE/PFD copolymer has a mole ratio of TFE/PFD of 13%/87% or 35%/65%, and has a permeability 1-2 magnitudes higher than that of said bulk polymer membrane.

5. The method, as recited in claim 1, wherein in the step (d), the predetermined temperature for baking said bonded membrane is 100-240° C.

6. The method, as recited in claim 3, wherein in the step (d), the predetermined temperature for baking said bonded membrane is 100-240° C., wherein said bonded membrane has a thickness of 0.005-0.05 mm after drying.

7. The method, as recited in claim 1, wherein said organic solution of PTFE particulate dispersion is prepared by 60% by weight of PTFE particles with 0.05-5 μm in particle size dispersed in water and wetting agent, which is baked at a temperature between 120-350° C. to form a coalesced porous network.

* * * * *